United States Patent [19]

Taniguchi et al.

[11] 4,342,568
[45] Aug. 3, 1982

[54] REFUSE DISPOSAL APPARATUS

[75] Inventors: Koichi Taniguchi, Inuyama; Kiyomi Niwa, Ogaki; Tadaaki Siraisi, Nagoya, all of Japan

[73] Assignee: Tokyo Shibaura Denki Kabushiki Kaisha, Kawasaki, Japan

[21] Appl. No.: 169,352

[22] Filed: Jul. 16, 1980

[30] Foreign Application Priority Data

Jul. 20, 1979 [JP] Japan .................................. 54-92855
Jul. 23, 1979 [JP] Japan .................................. 54-94009
Aug. 14, 1979 [JP] Japan ................................. 54-103317

[51] Int. Cl.³ .............................................. C10J 3/00
[52] U.S. Cl. ..................................... 48/111; 48/192; 48/197 A; 4/320; 4/322; 4/449; 210/179; 210/180; 210/603; 210/614; 431/89; 435/316
[58] Field of Search ................. 48/111, 209, 197 A, 48/192; 210/179, 180, 603, 614, 120, 219; 435/167, 316, 289, 287, 801; 431/44, 89; 4/DIG. 12, 449, 319–322, 111.1, 111.6

[56] References Cited

U.S. PATENT DOCUMENTS

| 691,365 | 1/1902 | Dittler | 4/321 |
|---|---|---|---|
| 1,732,775 | 10/1929 | Shaver | 4/319 |
| 2,449,185 | 9/1948 | Unger | 431/44 |
| 2,724,837 | 11/1955 | McPherson | 4/319 |
| 3,338,826 | 8/1967 | Kramer | 210/120 |
| 3,629,099 | 12/1971 | Gahmberg et al. | 4/321 |
| 4,157,958 | 6/1979 | Chow | 48/111 |
| 4,172,034 | 10/1979 | Carlsson et al. | 210/219 |
| 4,209,303 | 6/1980 | Ricks | 48/209 |
| 4,238,337 | 12/1980 | Peters et al. | 210/180 |

FOREIGN PATENT DOCUMENTS

| 1283763 | 11/1968 | Fed. Rep. of Germany | 210/219 |
|---|---|---|---|
| 40-16638 | 6/1965 | Japan . | |
| 48-3667 | 1/1973 | Japan . | |
| 51-76598 | 6/1976 | Japan . | |
| 621746 | 4/1949 | United Kingdom . | |
| 695322 | 8/1953 | United Kingdom . | |
| 764294 | 12/1956 | United Kingdom . | |
| 812616 | 4/1959 | United Kingdom . | |
| 913072 | 12/1962 | United Kingdom . | |
| 925891 | 5/1963 | United Kingdom . | |
| 926906 | 5/1963 | United Kingdom . | |
| 1206886 | 9/1970 | United Kingdom . | |

OTHER PUBLICATIONS

"Methods for Methane Fermentation; Use of Household Refuse as Raw Material", by Odawara, *Methane Fermentation Techniques and Applications*, pp. 5-1 to 5-12.

"Methane Fermentation Vessel Utility Solar Heat", by Uehara et al., *Clean Japan*, vol. 18, 9/79, pp. 28-31.

Primary Examiner—S. Leon Bashore, Jr.
Assistant Examiner—Michael Goldman
Attorney, Agent, or Firm—Cushman, Darby & Cushman

[57] ABSTRACT

Disclosed is a refuse disposal apparatus in which refuse fed into a fermenting vat can be disposed by subjecting the refuse to methane fermentation, the fermenting vat including a heating device for heating the refuse in the fermenting vat to a proper temperature for accelerated methane fermentation, and the refuse being agitated by an agitating device in the fermenting vat, so that methane produced in the fermenting vat by the methane fermentation may be externally collected by means of a gas collecting pipe for use as an everlasting heat source, and that sludge produced by the methane fermentation of the refuse in the fermenting vat may be discharged to the outside through a discharge pipe for use as fertilizer.

7 Claims, 9 Drawing Figures

REFUSE DISPOSAL APPARATUS

This invention relates to a refuse disposal apparatus capable of disposing of refuse while producing methane.

Generally known is the methane fermentation method in which anaerobic bacteria are caused to act on and decompose organic matter, thereby producing methane. However, there have not yet been developed any refuse disposal apparatus suited for disposing of daily household refuse while continuously producing methane by subjecting the refuse to methane fermentation, and the advent of such apparatus has been a long-cherished desire.

To meet such demand, a wide variety of household refuse disposal apparatus have hitherto been proposed. There have not, however, been developed any apparatus that can quickly dispose of refuse and provide methane as an everlasting home-use heat source.

The object of this invention is to provide a refuse disposal apparatus free from the above-mentioned drawbacks of the prior art apparatus and capable of continuously subjecting successively produced household refuse to quick and stable methane fermentation and collecting methane which can be used as everlasting fuel.

In order to attain the above object, the refuse disposal apparatus of this invention comprises a fermenting vat for subjecting refuse supplied thereto to methane fermentation, the fermenting vat being covered with an adiabatic wall, a heating device for heating the refuse in the fermenting vat, an agitating device for agitating the refuse in the fermenting vat, an inlet device for supplying the fermenting vat with the refuse, gas collecting means for taking out from the fermenting vat methane produced as a result of the methane fermentation, and discharge means for taking out from the fermenting vat sludge produced as a result of the methane fermentation.

Having the heating device to heat the refuse in the fermenting vat, the refuse disposal apparatus of the invention with the above-mentioned construction can be so designed that the temperature of the refuse may be adjusted to a proper value by means of the heating device to accelerate methane fermentation. Accordingly, the apparatus of this invention may be used as a household apparatus with which refuse can be successively cast into the fermenting vat to be quickly decomposed and methane produced as a result of such action can be used as an everlasting heat source.

Furthermore, sludge obtained as a result of the aforesaid methane fermentation can be taken out from the fermenting vat to be utilized as fertilizer for private vegetable gardens.

This invention can be more fully understood from the following detailed description when taken in conjunction with the accompanying drawings, in which.

Figure 1:
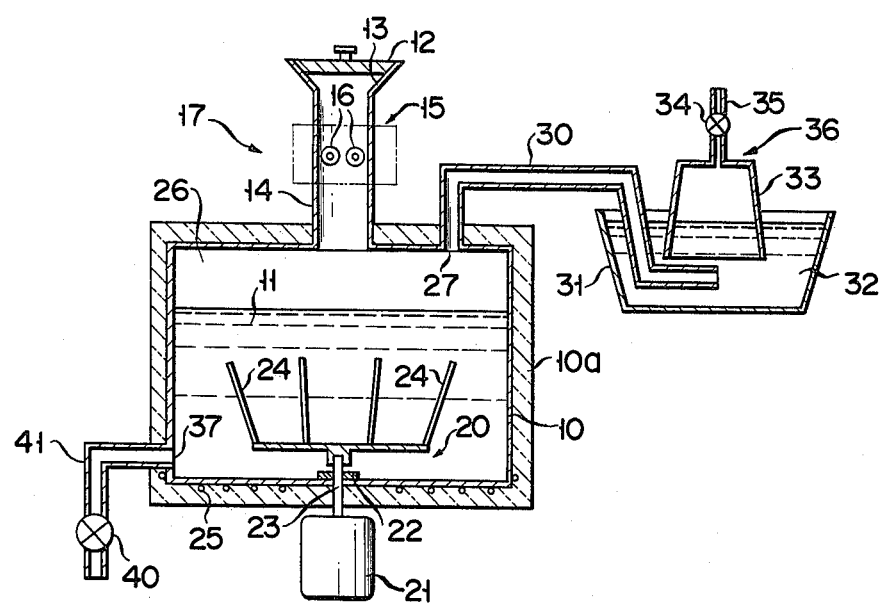
FIG. 1 is a front view in cross section showing a refuse disposal apparatus according to a first embodiment of this invention.

Now there will be described a first embodiment of the refuse disposal apparatus of this invention. In FIG. 1, a fermenting vat 10 is supplied with refuse 11, including garbage and other organic matter, and a proper quantity of water, and the refuse 11 is subjected to methane fermentation in the fermenting vat 10. As a result, methane is produced to change the refuse 11 into sludge as the fermentation process advances. The "garbage" means any organic matter including pieces of vegetables, fish, meat, etc., and the "other organic matter" means organic materials such as paper, grass, leaves, etc., both being capable of undergoing methane fermentation, naturally. The fermenting vat 10 is covered with an adiabatic wall 10a, and is provided with a refuse inlet tube 14 having at its top end a refuse inlet 13 closed with an openable cover 12. The bottom end of the inlet tube 14 opens into the interior of the fermenting vat 10 across the top wall of the vat 10. The middle portion of the inlet tube 14 is fitted with a crusher 15 enclosed in a frame represented by a chain line. While the crusher may be of various types, the crusher 15 of FIG. 1 is simple in construction, having crushing rollers 16 driven by a motor (not shown). Refuse which is cast, usually with water, through the inlet 13 is fractionized by the crusher 15, and then fed into the fermenting vat 10. The inlet tube 14 and the crusher 15 constitute inlet means for feeding refuse into the fermenting vat 10. Further, an agitating device 20 is disposed in the fermenting vat 10. The agitating device 20 is provided with a motor 21 disposed under the fermenting vat 10, and an agitator 24 attached to the top end of a shaft 23 of the motor 21 which penetrates the bottom wall of the fermenting vat 10 and a seal member 22. The refuse 11 collected in the fermenting vat 10 is agitated continuously during methane fermentation or intermittently as required by means of the agitator 24 which is driven by the motor 21.

On the outside face of the bottom of the fermenting vat 10, there is disposed a heating device, e.g. an electric heater 25. The electric heater 25 is used for heating the refuse 11 in the fermenting vat 10 so that the refuse 11 may be maintained at a proper temperature suited for fermentation. Generally, there are two temperature ranges suitable for methane fermentation; a middle-temperature range of 33° C. to 38° C. and a high-temperature range of 51° C. to 55° C. If the refuse 11 is maintained within the middle-temperature range, methane fermentation by methane bacteria called middle-temperature bacteria is accelerated. If the refuse 11 is maintained within the high-temperature range, on the other hand, methane fermentation by methane bacteria called high-temperature bacteria is encouraged. The decomposition-digestion time in the methane fermentation of the refuse 11 varies between these two temperature ranges. The decomposition-digestion time for the high-temperature range may be as short as 1/2.5 to ⅓ of that for the middle-temperature range. In order to maintain the refuse 11 at a temperature within either of those temperature ranges, the electric heater 25 is controlled by means of a conventional temperature control device (not shown) utilizing bimetal, for example.

A space over the refuse 11 in the fermenting vat 10 is called a gas pool chamber 26, in which methane produced in the fermenting vat 10 is collected. Methane in the chamber 26 is discharged from the other end of a gas collecting means or gas collecting pipe 30 immersed in water 32 contained in a water tank 31 through the gas collecting tube 30 one end of which is coupled to a gas collecting port 27 bored through the top wall of the fermenting vat 10, and is stored in a gas tank 33. As illustrated, the gas tank 33 has its opening side immersed in the water 32, and methane stored in the space inside the gas tank 33 is discharged for use through a combustion nozzle 35 communicating with the inside space and having a flow control valve 34 in the middle. The gas tank 33, flow control valve 34, combustion nozzle 35, and water tank 31 constitute a combustor 36. A sludge discharge port 37 at the lower portion of the fermenting vat 10 is fitted with discharge means or a discharge pipe 41 having a switching valve 40 at the middle portion thereof. The discharge pipe 41 is used for carrying out sludge obtained from the refuse as a result of methane fermentation.

Now there will be described the function or operation of the refuse disposal apparatus shown in FIG. 1. Usually, the apparatus of FIG. 1 is disposed in a kitchen, preferably in the vicinity of a sink. The cover 12 is taken off, and refuse produced in the kitchen, along with water, is cast into the inlet tube 14 through the refuse inlet 13. The refuse is fractionized into suitable size for methane fermentation by the action of the crushing rollers 16, and fed into the fermenting vat 10. When the cover 12 is restored, the fermenting vat 10 is hermetically sealed to encourage anaerobic bacteria. In this state, the electric heater 25 is energized, and the refuse 11 is maintained at a temperature suitable for methane fermentation by means of a temperature control device (not shown). The moment the electric heater 25 is energized, the motor 21 is driven, and the agitator 24 starts agitating the refuse 11 coexisting with water. When this state keeps on, the refuse 11 undergoes fermentation by methane bacteria which has been contained in air. As a result, the refuse 11 is decomposed to produce methane, and the remaining portion of the refuse 11 becomes sludge. Broadly, the fermentation is performed in two steps. In a first step, organic matter is decomposed into low molecular substances. Typical examples of such action includes an action to decompose protein with molecular weight of 200,000 to 300,000 into an amino acid with molecular weight of 200, as well as actions to change starch and fat into grape sugar and fatty acid, respectively. In a second step, the products obtained in the first step are decomposed into methane and carbon dioxide. The basic reaction in the second step is given by $$2C + 2H_2O = CH_4 + CO_2.$$

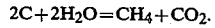

Approximately 70% of gas produced according to this equation is methane, and approximately 29% is carbon dioxide gas. The methane is collected in the gas pool chamber 26. If the decomposition advances so far that the gas pressure inside the gas pool chamber 26 exceeds the water pressure at the other end of the gas collecting pipe 30, the gas in the gas pool chamber 26 is discharged through the gas collecting pipe 30 into the gas tank 33, where it is stored. In this case, the gas tank 33 and the gas pool chamber 26 of the fermenting vat 10 are shut off from the atmosphere by the water tank 31, and the methane in the gas tank 33 is burnt by the combustion nozzle 35. The combustion nozzle 35 is set at every convenient spot in a home, and the methane is utilized for various home-service heat sources. The refuse in the fermenting vat 10 is changed into sludge at the end of methane fermentation, and the sludge, which is substantially entirely discharged from the fermenting vat 40 through the discharge pipe 41 by opening the switch valve 40, can be used as fertilizer for private vegetable gardens, for example. According to the apparatus of this invention, therefore, disposal of refuse is greatly facilitated as compared with direct disposal of garbage. Since the refuse, during methane fermentation, is heated by the electric heater 25 and agitated in the fermenting vat 10 which is substantially hermetically sealed and thermally insulated, the methane fermentation is encouraged, and the production of the sludge is accelerated. Thus, by casting the refuse 11 into the inlet tube 14 after discharging the sludge, the disposal of refuse may be continuously performed to enable use of produced methane as an everlasting heat source.

Figure 2:
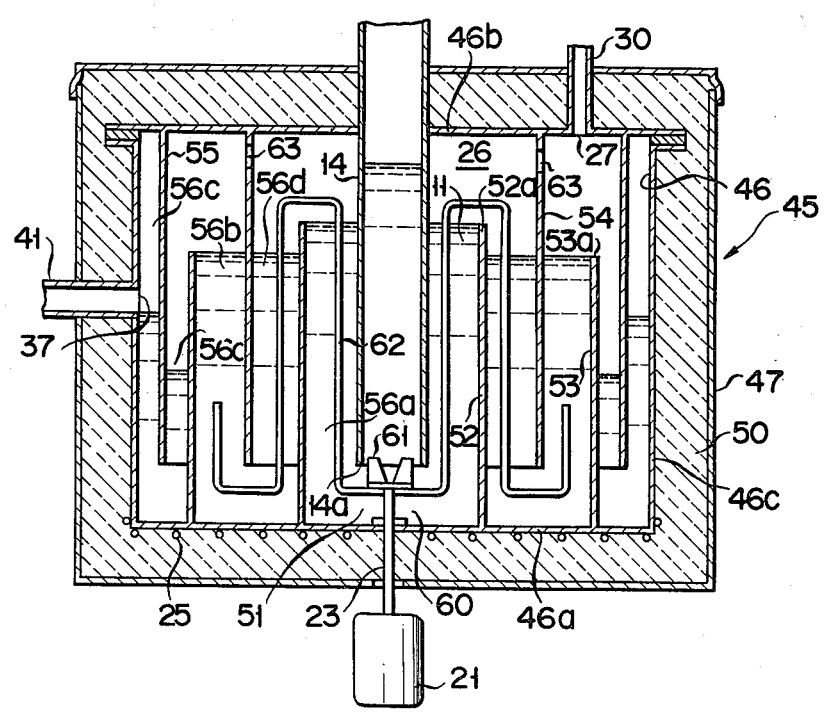
FIG. 2 is a front view in cross section showing a fermenting vat as used in a second embodiment of this invention.

Referring now to FIG. 2, there will be described a second embodiment of the refuse disposal apparatus of the invention. Since the difference between this second embodiment and the foregoing first embodiment lies only in the construction of the fermenting vat, FIG. 2 shows the fermenting vat alone. A fermenting vat 45 includes an inner vat section 46, an outer vat section 47, and an adiabatic wall 50 sandwiched between both these sections 46 and 47. The inner vat section 46 has a refuse receiving zone 51 formed in the center of the bottom thereof, and an inlet tube 14 extends downward at the central part of the fermenting vat 45. A bottom end opening 14a of the inlet tube 14 is immersed in refuse held in the refuse receiving zone 51. Erected on a bottom portion 46a of the inner vat section 46 are a first overflow tube 52 which surrounds the inlet tube 14 at a given space therefrom and a second overflow tube 53 which surrounds the tube 52 at a given space therefrom. First and second overflow sections 52a and 53a are formed respectively at the top ends of the first and second overflow tubes 52 and 53 so that the former is higher than the latter. Further, first and second partition walls 54 and 55 hang substantially vertically from a ceiling portion 46b of the inner vat section 46. The first partition wall 54 separates the first and second overflow tubes 52 and 53, while the second partition wall 55 separates the second overflow tube 53 from a peripheral wall 46c of the inner vat section 46. The suspended ends of the partition walls 54 and 55 are spaced from the bottom portion 46a of the inner vat section 46 so that the refuse 11 may move through the space therebetween. In the fermenting vat 45, a plurality of U-shaped trap chambers are defined continuously from the refuse receiving zone 51 to the peripheral wall 46c of the inner vat section 46, and outflow passages 56a, 56b and 56c and inflow passage 56d and 56e are defined between the zone 51 and the peripheral wall 46c. An agitating device 60 includes an electric motor 21 disposed under the fermenting vat 45, a shaft 23 of the motor 21 protruding into the inner vat section 46, and an impeller 61 and an agitator 62 attached to the upper end of the shaft 23. The impeller 61 is located correspondingly to the refuse receiving zone 51, and the agitator 62 is a meandering rod member which is vertically bent so as to extend through the outflow passage 56a, inflow passage 56d and outflow passage 56b. Moreover, a sludge discharge port 37 is formed in the substantially middle portion of the fermenting vat 45 so that it may communicate with the farthest outflow passage 56c from the refuse receiving zone 51. An air vent 63 at the upper portion of the first partition wall 54 connects a gas collecting inlet 27 with a gas pool chamber 26 except a portion corresponding to the outflow passage 56c out of a space defined over the refuse 11 in the fermenting vat 45.

In the case of the second embodiment, as described above, the refuse cast into the inlet tube 14 and crushed reaches the refuse receiving zone 51, where it is driven by the impeller 61 outwardly or in the horizontal direction of FIG. 2 to the outflow passage 56c by way of the first and second overflow sections 52a and 53a in order. The agitator 62 is driven by the electric motor 21 to rotate, thereby agitating the refuse 11 from the refuse receiving zone 51 before it passes through the second overflow section 53a and accelerating methane fermentation like the case of the first embodiment.

With use of the second embodiment, we may obtain the following effects. Since the bottom end of the inlet tube 14 is immersed in the refuse 11 in the fermenting vat 45, the interior of the fermenting vat 45 except the upper portion or space of the inlet tube 14 is cut off from the outside, and the outside air is prevented from entering into the gas pool chamber 26. The refuse 11 fed into the refuse receiving zone 51 goes up and down through the outflow passage 56a, inflow passage 56d, outflow passage 56b and inflow passage 56e in this order to reach the outflow passage 56c. Thereafter, the refuse 11 rises through the passage 56c, and is removed from the dirt discharge port 37 through a discharge pipe 41. Since the refuse 11 follows the aforesaid course, a portion of the refuse nearer to the closing stage of methane fermentation is located closer to the sludge discharge port 37. Thus, sludge is discharged from the sludge discharge port 37 in order of oldness, and no refuse capable of methane fermentation will be discharged. In such discharge of sludge, the atmosphere is prevented from entering into the fermenting vat 45 by the existence of the U-shaped trap chambers, so that the discharge pipe 41 may be left open. Since the overflow section 53a in the fermenting vat 45 is lower than the overflow section 52a, scum produced from a portion of refuse which has undergone methane fermentation flows toward the sludge discharge port 37 across the overflow sections 52a and 53a during the fermentation, never remaining in the fermenting vat 45 for long.

Figure 3:
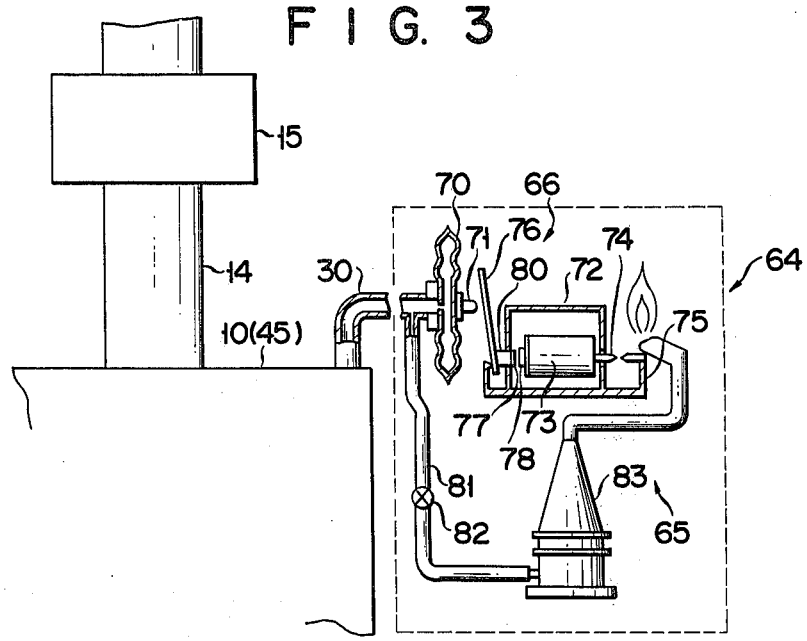
FIG. 3 is a front view partly in cross section showing an automatic firing combustor as used in the first and second embodiments of this invention.

FIG. 3 shows an automatic firing combustor 64 which is coupled to the gas collecting pipe 30 of the first and second embodiments described with reference to FIGS. 1 and 2, and automatically fires to burn methane when the methane pressure inside the gas pool chamber 26 in the fermenting vat 10 or 45 reaches a given level. A methane combustor 65 is fired by an automatic firing device 66. The automatic firing device 66 includes a diaphragm 70 attached to the distal end of the gas collecting pipe 30 and expanding and contracting in accordance with the pressure of methane led thereto by means of the gas collecting pipe 30, a presser 71 attached to the diaphragm 70 and moving in response to the expansion and contraction of the diaphragm, and a firing section 72 facing the presser 71 on the right-hand side thereof as in FIG. 3. The firing section 72 includes a piezoelectric element 73, electrodes 74 and 75 to which voltage produced by the piezoelectric element 73 is applied, a lever 76 driven to swing by the presser 71, a push member 80 attached to the lever 76, and operating plates 77 and 78 facing the push member 80 and the piezoelectric element 73.

When the pressure of methane introduced into the diaphragm 70 through the gas collecting pipe 30 reaches a given level, the lever 76 is pushed by the expanded diaphragm 70 and the presser 71 to swing clockwise in FIG. 3, and the operating plates 77 and 78 run against each other to apply pressure to the piezoelectric element 73, thereby causing high voltage produced from the piezoelectric element 73 to induce spark discharge between the electrodes 74 and 75. The combustor 65 includes a conduit 81 diverging from the gas collecting pipe 30, a switching valve 82 attached to the conduit 81, and a burner 83 attached to the forward end of the conduit 81. The switching valve 82 is opened in response to the operation of the automatic firing device to spout methane from the tip end of the burner 83 when the pressure inside the diaphragm 70 reaches a given level to expand the diaphragm 70 to a predetermined degree.

As is evident from the above description, the automatic firing combustor 64 is so constructed that when the gas pressure inside the fermenting vat 10 or 45 reaches a given level, the automatic firing device 66 and combustor 65 operate automatically, and sparks produced between the electrodes 74 and 75 act on and burn methane which is spouted from the burner 83. The methane burnt in this manner may be used for heating water in a hot-water tank (not shown), for example.

Thus, according to this invention, there may be obtained a refuse disposal apparatus suited for the disposal of refuse, especially household refuse. With the apparatus of the invention, refuse is changed into sludge by methane fermentation so that it may be utilized as fertilizer. In other words, the disposal of the refuse and final products obtained therefrom is facilitated. Further, successively produced refuse can be handled continuously by heating the refuse to accelerate methane fermentation, so that methane obtained by such methane fermentation can be used as everlasting fuel.

Figure 4A:
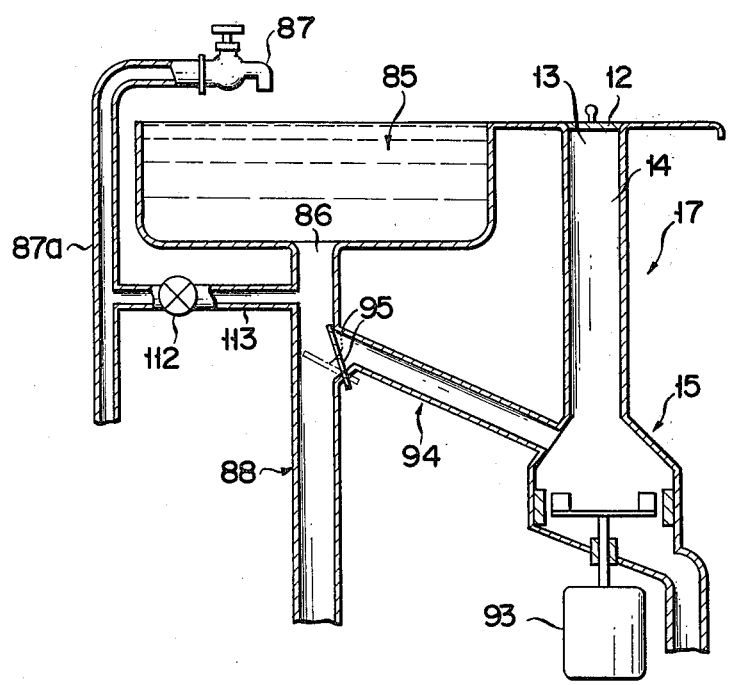
FIG. 4 is a front view in cross section showing a third embodiment of this invention, FIG. 4A being a front view in cross section showing a fourth embodiment of this invention.
Figure 4:
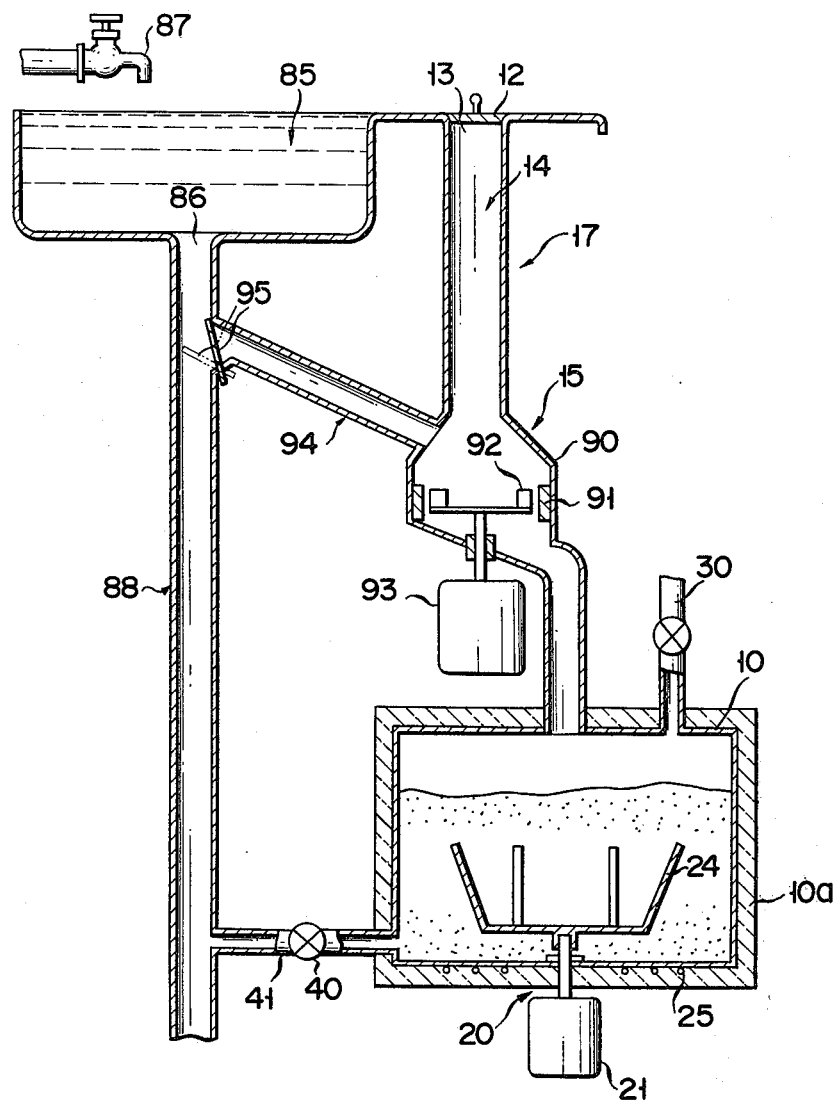
Figure 7:
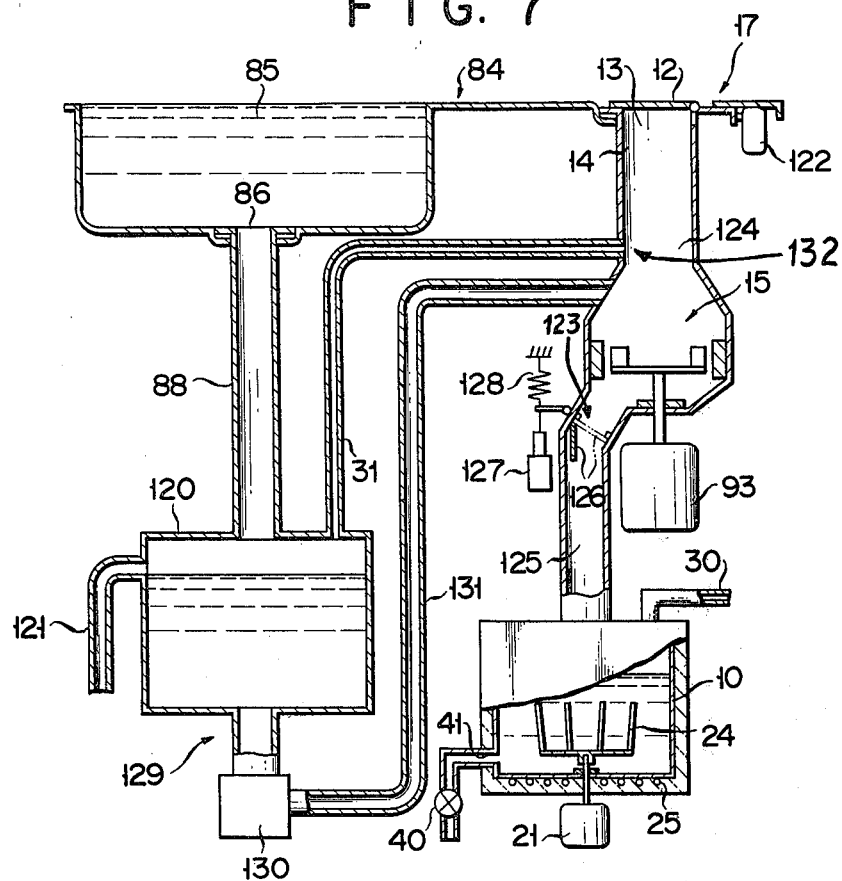
FIG. 7 is a front view partly in cross section showing a fifth embodiment of this invention.

FIGS. 4 and 7 show apparatus for supplying refuse and water to the fermenting vats 10 and 45 of the refuse disposal apparatus of FIGS. 1 and 2. The apparatus of these types are conveniently used in combination with household sink stands. Since either of the fermenting vats 10 and 45 can be used with the apparatus of FIGS. 4 and 7, only the fermenting vat 10 is shown in these drawings. Further, the section for the removal of methane from the fermenting vat 10 is represented by the gas collecting pipe 30 alone, and the means for burning the removed methane is omitted since it resembles the ones used with the apparatus of FIGS. 1 and 2.

Figure 5:
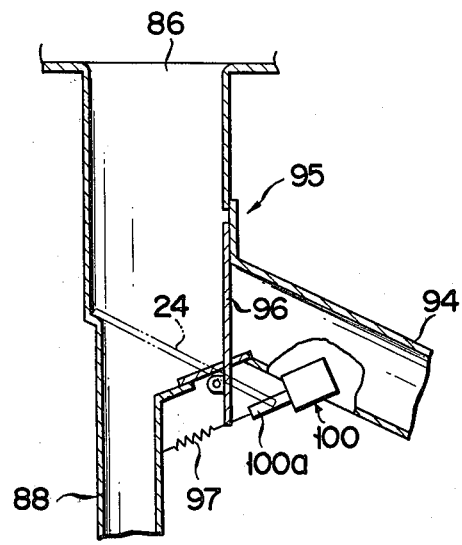
FIG. 5 is a view for explaining the operation of a selector valve as shown in FIGS. 4 and 5.
Figure 6:
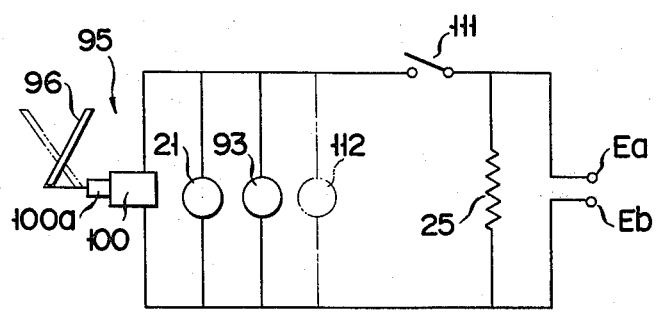
FIG. 6 is an electrical circuit diagram as used in the apparatus of FIG. 4.

In a third embodiment shown in FIG. 4, a sink 85 of a sink stand 84 has an exhaust port 86, and a tap 87 of a hydrant is located above the sink 85. The exhaust port 86 is connected to a sewer system (not shown) by means of a drain pipe 88. The sink stand 84 is provided with a refuse inlet tube 14 which extends substantially vertically near the sink 85. The inlet tube 14 is fitted with a removable cover 12 at the top, and the bottom portion of the tube 14 is coupled to the fermenting vat 10 by means of a crusher 15. The crusher 15 includes a casing 90, a stationary cutter 91 disposed inside the casing 90, a rotary cutter 92, and an electric motor 93 for rotating the rotary cutter 92. A discharge pipe 41 through which sludge is taken out from the fermenting vat 10 joins the drain pipe 88. If the sludge is separately removed for some use, however, the discharge pipe 41 need not to be joined with the drain pipe 88. The upper portion of the drain pipe 88 which communicates with the exhaust port 86 of the sink 85 and the upper portion of the casing 90 of the crusher 15 located above the stationary cutter 91 and rotary cutter 92 are coupled by means of a headrace 94. In this case, the headrace 94 declines to the crusher 15. At the diverging point between the headrace 94 and the drain pipe 88, there is selector means or a selector valve 95 which allows water from the sink 85 to flow through only one of the pipes 88 and 94. The inlet tube 14, crusher 15, headrace 94, and selector valve 95 form an inlet device 17 for refuse. FIG. 5 shows the selector valve 95 in detail. A selector plate 96 pivotally mounted on the diverging point between the drain pipe 88 and headrace 94 closes the headrace 94 with the aid of a spring 97 with one end fixed on the drain pipe side, as shown in FIG. 5. When excited, an electromagnetic solenoid 100 attached to the headrace 94 swings the selector plate 96 counterclockwise against the biasing force of the spring 97 by means of a plunger 100a (as represented by chain line), thereby closing the drain pipe 88. Thus, water flowing down from the sink 85 is led to the crusher 15 by means of the headrace 94. FIG. 6 shows an electric circuit used with the apparatus of FIG. 4. Power source terminals Ea and Eb are connected with the heater 25 to heat the fermenting vat 10. When a switch 111 is closed, the motor 93 for the crusher 15, the motor 21 for the agitating device 20, and the electromagnetic solenoid 100 for the selector valve 95 are connected in parallel with the heater 25. The switch 111 is attached to the sink stand 84 or some other easy-to-operate, safe place in the vicinity thereof.

In the embodiment of FIG. 4 constructed in the aforementioned manner, the electric heater 25 is energized until the switch 111 is closed, only warming the interior of the fermenting vat 10. Accordingly, the selector plate 96 closes the headrace 94 and opens the drain pipe 88 by means of the action of the spring 97. As a result, the water discharged from the sink 85 flows away to the sewer through the drain pipe 88. When the switch 111 is closed in this state, the electric motors 93 and 21 and the electromagnetic solenoid 100 are supplied with electric power, and the rotary cutter 92 of the crusher 15 and the agitator 24 in the fermenting vat 10 start rotating, the electromagnetic solenoid 100 swings the selector plate 96 by means of the plunger 100a, and all the water from the sink 85 is introduced into the crusher 15. When the cover 12 of the inlet tube 14 is opened and garbage or other suitable refuse is cast into the inlet tube 14 in this state, the refuse is mixed with water fed through the headrace 94 in the crusher 15, effectively crushed by the rotary cutter 92, and then fed into the fermenting vat 10. Resembling the cases of the first and second embodiments, description of the subsequent operations of the fermenting vat 10 and other sections is omitted.

According to this third embodiment, the refuse may be crushed in water or broken to small pieces rapidly and fully while floating the refuse on the water by utilizing the water fed from the sink 85 of the sink stand 84. Moreover, by mixing the refuse with water as aforesaid, clog may be prevented from being caused while the refuse is fed into the fermenting vat 10. If no refuse is cast, all the water flowing down from the sink 85 is carried to the sewer by opening the switch 111 (FIG. 6). Since the switch 111, when closed, simultaneously energizes and actuates the selector plate 96 and crusher 15, the operation of the refuse disposal apparatus is facilitated, and wrong operation is prevented. Further, since the headrace 94 can be closed by opening the switch 111, excessive water supply to the fermenting vat 10, as well as supply of any neutral detergent used in the sink 85 to the fermenting vat 10, may be prevented effectively.

A fourth embodiment shown in FIG. 4A is a modification of the embodiment of FIG. 4. This modified embodiment differs from the embodiment of FIG. 4 in that a service pipe 87a coupled to the tap 87 is connected with the drain pipe 88 by means of a connecting pipe 113 having a valve 112, the connecting pipe 113 being coupled to the drain pipe 88 at a level above the diverging point between the headrace 94 and the drain pipe 88. With this connecting pipe 113, water may be fed directly from the service pipe 87a, without operating the tap 87 each time refuse is cast into the inlet tube 14, by energizing the valve 112 simultaneously with the selector valve 95 and crusher 15. In the wiring diagram of FIG. 6, the valve 112 is represented by chain line.

FIG. 7 shows a fifth embodiment of the invention. The refuse disposal apparatus of this embodiment differs from the foregoing embodiments mainly in that it is further provided with a feed-water supply system to supply the fermenting vat with water via the crusher and a switching valve disposed between the crusher and fermenting vat. Since the crusher, fermenting vat and the device for burning methane are the same as the ones shown in FIG. 3, detailed description of these components is omitted, and the methane combustor is not shown.

In FIG. 7, an exhaust port 86 of a sink 85 built in a sink stand 84 is fitted with a drain pipe 88 extending downward, the bottom end of the drain pipe 88 opening into a drainage tank 120. The drainage tank 120 is provided with an overflow passage 121. In the vicinity of the sink 85 of the sink stand 84, there is installed an inlet tube 14 which extends substantially vertically, communicating with a fermenting vat 10 through a crusher 15. An openable cover 12 is fitted on the top end of the inlet tube 14, and interlocking means or a microswitch 122 is driven by the action of the cover 12. The inside space of the inlet tube 14 is divided by a switching valve 123 into two sections; an upper space 124 containing the crusher 15 and a lower space 125 thereunder. The switching valve 123 is provided with a swinging plate 126, an electromagnetic solenoid 127 which, when energized, swings the swinging plate 126 to allow the upper and lower spaces 124 and 125 to communicate, and a spring 128 to cut off the communication between the spaces 124 and 125 by swinging back the swinging plate 126 when the electromagnetic solenoid 127 is deenergized. A pump 130 disposed under the drainage tank 120 feeds water in the drainage tank 120 into the upper space 124 of the inlet tube 14 by way of a water passage 131. The drainage tank 120, pump 130, water passage 131, and overflow passage 121 form the feed-water supply system 129. Since an overflow passage 132 is coupled to an opening at a level just above the upper space 124, the water level in the upper space 124 will never be above the opening.

Figure 8:
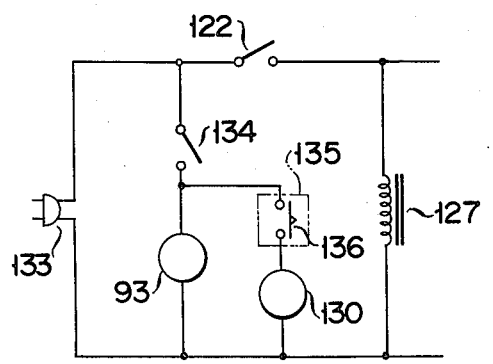
FIG. 8 shows an electrical circuit as used in the apparatus of FIG. 7.

FIG. 8 shows electric wiring of the apparatus of FIG. 7. Electric power supplied from a power source plug 133 is supplied directly to an electric motor 93 for the crusher and to a pump 130 through a timer 135 when an operating switch 134 attached to the sink stand 84 or any other suitable place in the vicinity thereof is closed. The power supplied from the power source plug 133 is further supplied via the microswitch 122 to the electromagnetic solenoid 127 to swing the swinging plate 126. The microswitch 122 is turned on and off when the cover 12 is closed and opened, respectively. The timer 135, which has a contact circuit 136 connected in series with the pump 130, closes the timer switch 136 only for a given time after it is energized.

Now there will be described the operation of the embodiment of FIG. 7. First, when the cover 12 is taken off, the microswitch 122 is turned on, the electromagnetic solenoid 127 is excited, and the communication between the upper and lower spaces 124 and 125 is cut off by a swing of the swinging plate 126 of the switching valve 123. At this time, refuse produced in e.g. a home is cast into the inlet tube 14. Since the lower space 125 is closed, the cast refuse is stored in the upper space 124. When the operating switch 134 (FIG. 8) is closed during or after such refuse casting, the electric motor 93 of the crusher 15 is driven to start crushing of the refuse, and the pump 130 is driven for a given time to cause the drainage in the drainage tank 120 to be poured into the upper space 124. Accordingly, like the case of the third and fourth embodiments, the refuse is crushed in water in the crusher 15, and rapidly broken to fine pieces. When the operating swith 134 (FIG. 8) is turned off and the cover 12 is restored to turn the microswitch 122 off after the refuse is fully crushed, the operation of the crusher 15 is stopped, the excitation of the electromagnetic solenoid 127 is interrupted, and the communication between the upper and lower spaces 124 and 125 is recovered. As a result, the crushed refuse, along with water, falls down into the fermenting vat 10, and undergoes methane fermentation. Resembling the cases of the foregoing embodiments, description of methane obtained from the refuse by such methane fermentation, as well as the construction of the combustor and the discharge and utilization of sludge produced as a result of the methane fermentation, is not repeated here. When the level of water in the upper space 124 reaches a given level, extra water is returned to the drainage tank 120 through the overflow passage 132. Thus, extremely abundant water will never flow into the fermenting vat 10.

According to the embodiment of FIG. 7, the use of the switching valve 123 for switching the communication between the upper and lower spaces 124 and 125, as well as the overflow passage 132 opening into the upper space 124, prevents water of a quantity exceeding a given quantity from being fed into the fermenting vat 10 while refuse is cast at a time. Further, the switching valve 123 practically keeps an offensive smell inside the fermenting vat 10 from leaking out from the inlet tube 14 while the refuse is being cast into the upper space 124, and also prevents the outside air from entering into the fermenting vat 10 through the inlet tube 14. Accordingly, there will be no possibility of methane's mixing with oxygen from the outside air to form an explosive gas mixture. Moreover, it will be possible to prevent retardation of methane fermentation which may be caused by the action of the outside air on anaerobic methane bacteria.

The members and control systems at the several sections in the embodiment of FIG. 7 are given only by way of example. Alternatively, for example, the switching valve 123 may be so designed as to operate independently of the action of the cover 12, or the level of water in the upper space 124 may be maintained at the given level by controlling the operation of the pump 130 by means of a level switch (not shown) disposed inside the upper space 124.

What we claim is:

1. A refuse disposal apparatus comprising:
    a fermenting vat, including a ceiling portion and a bottom portion, for subjecting refuse supplied thereto to methane fermentation, said fermenting vat being covered with an adiabatic wall;
    an inlet device for supplying said fermenting vat with the refuse, the inlet device including an inlet tube having a refuse inlet which extends through said ceiling portion and hangs down into the fermenting vat so that the lower end of the refuse inlet is immersed in the refuse in the fermenting vat, thereby forming in said fermenting vat a gas pool chamber which is cut off from air at said refuse inlet;
    a heating device for heating refuse within the fermenting vat;
    an agitating device for agitating refuse within the fermenting vat;
    gas collecting means for removing from the fermenting vat methane produced as a result of methane fermentation of refuse therein; and
    discharge means for removing from the fermenting vat sludge produced as a result of methane fermentation of the refuse,
    the fermenting vat including more than one spaced apart overflow tubes each of which surrounds said inlet tube and extends upwardly from the bottom portion of the fermenting vat but does not extend to the ceiling portion and one or more partition walls located in spaces defined by adjacent overflow tubes and protruding downward from the ceiling portion of the fermenting vat without protruding to the bottom portion, each overflow tube being longer than the adjacent overflow tube surrounding it, the adjacent overflow tubes and the interposed partition wall together forming at least one U-shaped trap, whereby refuse emerging from the inlet tube is forced to flow over the top of each overflow tube and through said at least one U-shaped trap toward said discharge means.

2. A refuse disposal apparatus according to claim 1 further comprising:
    a refuse crusher attached to said inlet tube,
    a headrace diverging from a drain pipe, which is coupled to an exhaust port of a sink of a sink stand, said headrace also being disposed near said inlet tube and communicating with the refuse inlet side of said crusher, and
    selector means for selectively causing water to flow from said drain pipe into said headrace.

3. A refuse disposal apparatus according to claim 2, wherein said switch further includes means for (a) operating the water passage selector means so as to cause the headrace and drain pipe to communicate with each other and (b) simultaneously operating the refuse crusher.

4. A refuse disposal apparatus according to claim 1, further including
    a switching valve attached to said inlet tube and airtightly separating the inside space of said inlet tube into upper and lower spaces and allowing said upper and lower spaces to selectively communicate, and a crusher disposed inside said upper space for crushing the refuse supplied from said refuse inlet.

5. A refuse disposal apparatus according to claim 4, wherein said inlet device further includes a cover for opening and closing said refuse inlet tube, and interlocking means for (a) cutting off the communication between said upper and lower spaces when said cover is opened by said switching valve and (b) recovering said communication when said cover is closed.

6. A refuse disposal apparatus according to claim 4 further comprising a feed-water supply system pouring water into said upper space when said upper space is cut off from said lower space by said switching valve.

7. A refuse disposal apparatus according to claim 6 further comprising a passage coupled to a portion of said inlet tube defining said upper space, whereby the water poured into said upper space is caused to overflow when the quantity of said water becomes excessive.

* * * * *